(12) United States Patent
Spicer et al.

(10) Patent No.: US 9,597,648 B2
(45) Date of Patent: *Mar. 21, 2017

(54) NON-SPHERICAL DROPLET

(71) Applicant: The Procter & Gamble Company, Cincinnati, OH (US)

(72) Inventors: Patrick Thomas Spicer, Cincinnati, OH (US); Marco Caggioni, Cincinnati, OH (US); Jessica Lenis-Abril, Elmhurst, NY (US); Alexandra Victoria Bayles, Millersville, MD (US)

(73) Assignee: The Procter & Gamble Company, Cincinnati, OH (US)

( * ) Notice: Subject to any disclaimer, the term of this patent is extended or adjusted under 35 U.S.C. 154(b) by 362 days.

This patent is subject to a terminal disclaimer.

(21) Appl. No.: 14/056,197

(22) Filed: Oct. 17, 2013

(65) Prior Publication Data

US 2015/0111863 A1 Apr. 23, 2015
US 2016/0243514 A9 Aug. 25, 2016

Related U.S. Application Data

(60) Provisional application No. 61/715,100, filed on Oct. 17, 2012.

(51) Int. Cl.
| | | |
|---|---|---|
| *B01F 17/00* | (2006.01) | |
| *A61K 8/06* | (2006.01) | |
| *A61K 8/02* | (2006.01) | |
| *A61Q 19/00* | (2006.01) | |
| *A61K 8/31* | (2006.01) | |
| *A61K 8/46* | (2006.01) | |
| *A61K 8/92* | (2006.01) | |

(52) U.S. Cl.
CPC ............ *B01F 17/00* (2013.01); *A61K 8/0204* (2013.01); *A61K 8/06* (2013.01); *A61K 8/064* (2013.01); *A61K 8/066* (2013.01); *A61K 8/31* (2013.01); *A61K 8/463* (2013.01); *A61K 8/466* (2013.01); *A61K 8/922* (2013.01); *A61Q 19/00* (2013.01); *A61K 2800/10* (2013.01)

(58) Field of Classification Search
CPC .......... A61K 8/31; A61K 8/463; A61K 8/466; A61K 8/922; A61K 8/0204; A61K 8/066; A61K 8/064; A61K 2800/10; A61Q 19/00; B01F 17/00
See application file for complete search history.

(56) References Cited

U.S. PATENT DOCUMENTS

| | | | |
|---|---|---|---|
| 5,955,091 A | 9/1999 | Hansenne et al. | |
| 6,057,386 A | 5/2000 | Kobayashi et al. | |
| 6,258,857 B1 | 7/2001 | Iijima et al. | |
| 6,410,605 B1 | 6/2002 | Funada et al. | |
| 7,074,335 B2 | 7/2006 | Berg et al. | |
| 7,351,755 B2 | 4/2008 | Hayashi | |
| 7,776,927 B2 | 8/2010 | Chu et al. | |
| 8,158,571 B2 | 4/2012 | Alonso et al. | |
| 8,183,540 B2 | 5/2012 | Bain et al. | |
| 8,637,324 B2 | 1/2014 | Pamula et al. | |
| 2002/0160928 A1 | 10/2002 | Smerznak et al. | |
| 2005/0000028 A1 | 1/2005 | Baker et al. | |
| 2005/0276831 A1 | 12/2005 | Dihora et al. | |
| 2006/0127338 A1 | 6/2006 | Kobayashi et al. | |
| 2007/0148437 A1 | 6/2007 | Mueller-Schulte | |
| 2010/0150975 A1 | 6/2010 | Dihora et al. | |
| 2010/0326071 A1 | 12/2010 | Gracias et al. | |
| 2010/0329982 A1 | 12/2010 | Lendlein et al. | |
| 2011/0229545 A1 | 9/2011 | Holtze et al. | |
| 2013/0184194 A1 | 7/2013 | Chen et al. | |

FOREIGN PATENT DOCUMENTS

| WO | WO 9525433 | 9/1995 |
|---|---|---|
| WO | WO 2007061032 | 5/2007 |

OTHER PUBLICATIONS

International search report and Written Opinion dated Apr. 29, 2014, U.S. Appl. No. 14/056,160, 8 pages.
International search report and Written Opinion dated Jun. 12, 2014, U.S. Appl. No. 14/056,160, 10 pages.
Carroll, Brendan Joseph, "The Equilibrium of liquid Drops on Smooth and Rough Circular Cylinders", Journal of Colloid and Interface Science, vol. 97, No. 1, Jan. 1984, pp. 195-200.
Velev et al., "Assembly of Latex Particles by using Emulsion Droplets as Templates. 2. Ball-like and Composite Aggregates", Langmuir 1996, vol. 12, pp. 2385-2391.
Manoharan et al., "Dense Packing and Symmetry in Small Clusters of Microspheres", Science, vol. 301, 2003, pp. 483-487.
Mitragotri et al., "Physical Approaches to Biomaterial Design", Nature Materials, vol. 8, 2009, pp. 15-23.
Mitchison et al., "Implications of a Poroelastic Cytoplasm for the Dynamics of Animal Cell Shape", Seminars in Cell & Development Biology 19, 2008, pp. 215-223.
Dendukuri et al., "The Synthesis and Assembly of Polymeric Microparticles using Microfluidics", Advanced Materials, vol. 21, 2009, pp. 1-16.
Bong et al., "Lock Release Lithography for 3D and Composite Microparticles", Lab on a Chip, vol. 9 (7), Apr. 2009, pp. 862-866.
Fredrick et al., "Factors Governing Partial Coalescence in Oil-in-water Emulsions", Advances in Colloid and Interface Science, vol. 153, 2010, pp. 30-42.
Py et al. "Capillary Origami: Spontaneous Wrapping of a Droplet with an Elastic Sheet", Physical review letters, Feb. 6, 2008, pp. 1-5.
Leong et al., "Surface Tension-driven Self-folding Polyhedra", Langmuir, 2007, vol. 23, No. 17, pp. 8747-8751.
Sacanna et al., "Lock and Key Colloids", Nature, vol. 464, Mar. 25, 2010, pp. 575-578.
Weber et al., ""Schizomorphic" Emulsion Copolymerization Particles", Macromolecular Rapid Communications, 2001, 32, pp. 1925-1929.
Shukla et al., "Investigation of W/O microemulsion droplets by contrast variation light scattering", PRAMANA Journal of Physics, vol. 65, Dec. 2005, pp. 1097-1108.
Shah et al., "Designer Emulsions using Microfluidics", Materials Today, vol. 11, No. 4, Apr. 2008, pp. 18-27.
U.S. Appl. No. 14/056,160, filed Oct. 17, 2013, Patrick Thomas Spicer et al.

*Primary Examiner* — Ali Soroush
*Assistant Examiner* — Genevieve S Alley
(74) *Attorney, Agent, or Firm* — James C Vago (57) ABSTRACT

Non-spherical liquid droplets comprising a liquid, an internal solid material defining the shape of the droplet, a benefit agent, and methods of making non-spherical liquid droplets.

16 Claims, 4 Drawing Sheets

NON-SPHERICAL DROPLET

FIELD OF THE INVENTION

The present invention relates to liquid droplets comprising internal solid material and to methods of making said liquid droplets.

BACKGROUND OF THE INVENTION

Benefit agents, such as perfumes, enzymes and the like are often delivered to a substrate in the form of a droplet or particle. Such delivery can be achieved by using a liquid droplet which can exist within another liquid or within the air, such as an aerosol for example. Another method is via a loaded solid carrier material such as zeolite or starch. In this case the benefit agent usually exists as a liquid which is applied to the carrier material and is absorbed within the solid particle. A final approach is via core-shell particles, in which the benefit agent is a component of a liquid core which is surrounded by a solid shell. However, there are a number of problems encountered when using these known methods.

Loaded carrier materials suffer from two issues. The first is the ability to attach to the substrate. Attachment often relies upon attractive forces such as charge attraction between the solid carrier material and the substrate. If the surface has a charge that is similar to that of the carrier material outer surface then attachment is unlikely. Secondly, even if attachment to the substrate should be successful, movement of the benefit agent from the carrier material to the substrate can be problematic. This is because the solid carrier material is attached to the substrate, and so the liquid absorbed into the carrier material may not be able to easily transfer as it is not in direct contact with the substrate.

Liquid droplets overcome some of the disadvantages of loaded carrier materials. Firstly, since they are liquid, they can attach to the substrate without the same requirement as for solid particles, such as charge attraction, etc. Attachment is facilitated by liquid-solid attachment, i.e. 'wetting'. Wetting' is essentially the extent to which a liquid can wet a solid, and is a function of the force of adhesion between a liquid and a solid. This type of adhesion is evident, for example, when droplets of a liquid form on a solid surface, e.g. water droplets on glass. Furthermore, the ability of the benefit agent to reach the substrate surface will also be improved. This is because when the droplet adheres to the substrate, the benefit agent can easily pass through the liquid and directly to the substrate surface. However, liquid droplets tend to be spherical. This results in a low surface area for initial contact to the substrate, especially if the substrate presents a low surface area to the droplet itself, such as a natural fiber (examples being hair or cotton fiber) or a synthetic fiber (examples being nylon or polypropylene). Hence, initial attachment tends to be problematic.

Core-shell particles comprise a solid outer shell and a liquid inner core comprising the benefit agent. These types of particle are often spherical, but can also be non-spherical hence providing a higher surface area for improved initial attachment and adhesion. However core-shell particles still suffer from the charge-based adhesion problems and transfer of benefit agent as those of loaded carrier material particles. For either solid particles or core-shell particles the contact area between particle and substrate is limited because solids tend not to deform much upon contacting a substrate. This is especially problematic when the substrate has a non-planar surface topography, such as a curved hair or fibre.

Thus, there remains a need in the art for a benefit agent delivery particle that at least partially overcomes the above-mentioned problems.

It has now been surprisingly found that a non-spherical liquid droplet comprising a solid material that defines the shape of the droplet overcomes the above-mentioned problems. The solid material allows the droplet to have a non-spherical shape, but since the droplet is liquid over its entire surface, optimal attachment to the substrate can be achieved due to the wetting of the substrate and spreading onto the substrate by the liquid droplet.

SUMMARY OF THE INVENTION

The present invention is to a non-spherical liquid droplet, wherein the liquid droplet comprises: a liquid; and an internal solid material, the internal solid material defining the shape of the droplet; and a benefit agent; and wherein the three-phase contact angle of the liquid on the internal solid material is less than 1°; and wherein, the liquid droplet has a yield stress of between 100 and 1,000,000 Pascals.

The present invention is also to a composition comprising an external liquid and the liquid droplet as described above, wherein the liquid droplet is immiscible with the external liquid.

The present invention is also to a method of depositing a benefit agent on a substrate comprising the steps of: (i) preparing a liquor comprising an external liquid and a non-spherical liquid droplet, wherein the droplet comprises; (a) a liquid; and (b) an internal solid material, the internal solid material defining the shape of the droplet; and (c) a benefit agent; and wherein the three-phase contact angle of the liquid on the internal solid material is less than 1°; and wherein, the liquid droplet has a yield stress of between 100 and 1,000,000 Pascals; and wherein, the liquid droplet is immiscible with the external liquid; and (ii) contacting the liquor with the substrate.

The present invention is also to a method for making a non-spherical droplet according to the present invention comprising the steps of: (i) mixing a first liquid composition comprising a molten ingredient having a yield stress of between 100 and 1,000,000 Pascals, the yield stress being measured at a temperature of 25° C. and a second liquid and a liquid benefit agent, wherein the first and second liquids and liquid benefit agent are mixed at a temperature above 50° C. to make a liquid droplet premix; (ii) preparing a channel, wherein the channel optionally comprises a third liquid, the third liquid being immiscible with the second liquid, and wherein the third liquid is flowing through the channel; (iii) drawing individual droplets of the liquid droplet premix into the channel, wherein the channel comprises a constriction to shape the droplet; (iv) passing the premix droplets into the constriction at a temperature of 50° C. or below so that the first liquid solidifies to produce liquid non-spherical droplets; (v) depositing the non-spherical liquid droplets into a composition comprising the third liquid, the third liquid being immiscible with the second liquid.

BRIEF DESCRIPTION OF THE DRAWINGS

FIG. 1 discloses examples of two-dimensional projections of three-dimensional non-spherical liquid droplets.

FIG. 2A depicts three phase contact angle measurement.

FIG. 2B depicts three phase contact angle measurement.

FIG. 2C depicts three phase contact angle measurement.

FIG. 3 disclose non-spherical droplets according to the present invention.

FIG. 4 discloses an exemplary droplet shape making means.

DETAILED DESCRIPTION OF THE INVENTION

The Non-Spherical Liquid Droplet

The present invention is to a non-spherical liquid droplet, wherein the liquid droplet comprises: a liquid; and an internal solid material, the internal solid material defining the non-spherical shape of the droplet; a benefit agent; and wherein the three-phase contact angle of the liquid on the internal solid material is less than 1°; and wherein the liquid droplet has a yield stress of between 100 Pascal and 1,000,000 Pascal, or even between 1000 Pascal and 100,000 Pascal, or even between 5000 and 10,000 Pascal.

The yield stress of the liquid droplet is measured at a temperature of 25° C. Without wishing to be bound by theory, the yield stress is a measure of the rheology of the liquid droplet. The yield stress is the point at which the liquid droplet, comprising both liquid and internal solid material, goes from being in a non-flowable state to a flowable state. The method for determining the yield stress is described in more detail below.

A spherical liquid droplet is a droplet in which every point on its surface is equidistant from its centre. It should be understood that the term 'equidistant' includes a standard degree of error of +/−2%. A non-spherical liquid droplet is a droplet that has any shape which is not spherical. Without wishing to be bound by theory, non-spherical liquid droplets are advantageous because they exhibit excellent attachment to the substrate due to the wetting effect of the liquid, but also exhibit excellent adherence to the substrate because of the large surface area of the non-spherical droplet.

Figure 1:
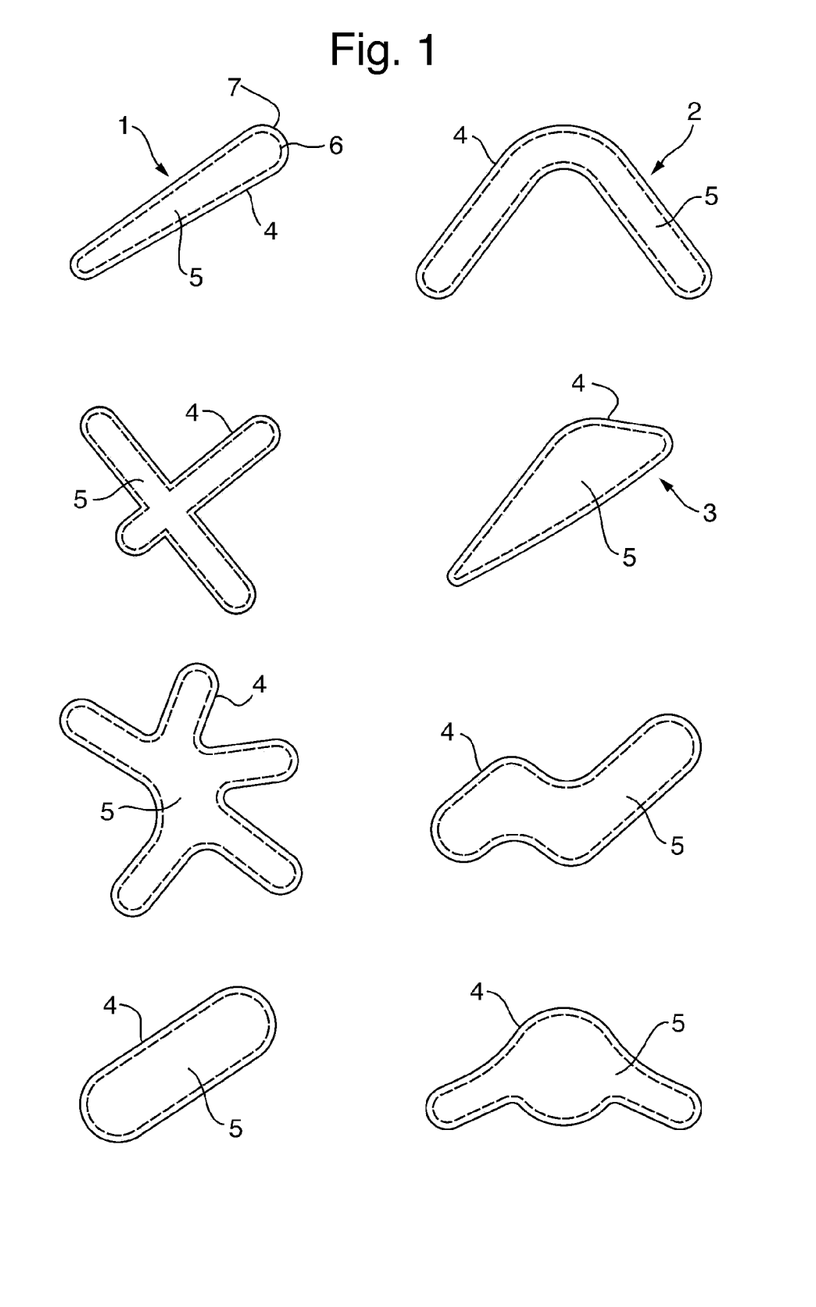

The non-spherical liquid droplet may be any non-spherical shape. A number of non-limiting examples can be seen in FIG. 1. The diagrams in FIG. 1 represent two-dimensional projections of three-dimensional non-spherical liquid droplets. Here the projected area is taken to mean the area of a two-dimensional projection of a three-dimensional object onto a flat plane such as an image provided when viewing a microscope slide where a 3D object is placed upon the slide, or a 3D object is sandwiched between a slide and a coverslip. The non-spherical droplet may be rod shaped (1). Alternatively, it may have an elongated, yet curved shape (2) or even a triangular or wedge shape (3).

A liquid droplet is understood to mean a droplet in which the entire outer surface of the droplet is liquid (4). Even if the droplet also comprises a solid component (5), to be a liquid droplet the solid component must be completely enclosed within the liquid part of the droplet (4). The distance between any point on the surface of the internal solid material (6) and the outer edge of the liquid droplet (7) may be at least 10 nanometers, or even at least 100 nanometers, or even at least 1 micron.

The liquid can be any suitable liquid. The liquid could be an oil or an aqueous liquid. Suitable liquids are described in more detail below. It should be noted that the materials used in the liquid, the internal solid material and the benefit agent are all different from one other. For example the liquid in the droplet and the benefit agent are not the same substance. The material used for the internal solid material and droplet liquid can be derived from the same source, for example both may be fatty alcohols, but at room temperature the fatty alcohol in the liquid is liquid and the fatty alcohol in the solid is solid. Hence, in this particular example, they will be different in terms of melting point.

The internal solid material can be any suitable solid material. The internal solid material can be porous or non-porous. Suitable internal solid materials are detailed below. The internal solid material may comprise at least 5%, or even at least 10%, or even at least 20%, or even at least 50% by volume of the droplet. The internal solid material may comprise at most 95% by volume of the liquid droplet. The person skilled in the art would know how to determine the percentage using known techniques.

The internal solid material defines the shape of the liquid droplet. A liquid droplet that does not comprise an internal solid material that defines the shape will seek to form a sphere because of the pressure exerted by its interfacial tension, γ, with any external fluid within which it exists (as in an emulsion, for example). The pressure exerted by the interfacial tension can be offset by an internal structure, such as an internal solid material, within the droplet, when the yield stress of the internal solid material matches or exceeds the pressure exerted by the interfacial tension, allowing the droplet to stably preserve a non-spherical shape. The deformed liquid droplet will remain stable as long as the force balance does not change. If the pressure exerted by the interfacial tension is increased, for example by dilution of the external liquid with a diluent, for example water, so as to exceed the yield stress of the droplet containing the internal solid material, the droplet will transform into a more compact shape, including a sphere or more curved form. Similarly the balance may be shifted if the yield stress of the droplet containing internal solid material is decreased, for example by heating to soften or melt the internal solid material while maintaining the same/similar pressure exerted by the interfacial tension. Other diluents can include an aqueous solution of surfactant, or an aqueous solution of polymer, or an aqueous dispersion of colloids or mixtures thereof. Without wishing to be bound by theory, the yield stress of the internal solid material contributes to the overall yield stress of the liquid droplet. Hence the internal solid material contributes to resisting deformation of the overall liquid droplet. It should be noted that the yield stress of the internal solid material will always be greater than that of the yield stress of the complete liquid droplet (comprising the internal solid material). The method for determining the yield stress is described in more detail below.

The liquid droplet comprises a benefit agent. A benefit agent is defined as a compound or ingredient that imparts a benefit, for example cleaning, coating, substrate restoration, colour change, reduced coefficient of friction or water repellency, sensorial, biological agents including enzymes, probiotics, prebiotics, medicament, nutraceutical or combinations thereof. The benefit agent is described in more detail below.

The liquid droplet has a three phase contact angle of the droplet liquid on the internal solid material of less than 1°, a condition termed "complete wetting." 'Wettability' is essentially the extent to which a liquid can wet a solid, and is a function of the force of adhesion between a liquid and a solid. Wetting is a fundamental physical property of a solid-liquid combination. In naturally non-wetting, or low wettability situations, wetting agents such as surfactants, polymers, or colloids can be added to modify a fluid's or solid's properties to allow wetting, between the two, that would not occur without additives. In the context of the present invention, the surface of the internal solid material is completely wetted by the droplet liquid. In other words, the surface of the internal solid material is not in contact with the environment external to the non-spherical liquid droplet. Only the outer surface of the liquid part of the non-spherical liquid droplet is in contact with the external environment.

Without wishing to be bound by theory, the three-phase contact angle is a measure of the capacity of the liquid to remain around the internal solid material and not dissociate from it. In a liquid external environment if the liquid component of the droplet does not completely wet the internal solid material, in order to achieve equilibrium, the droplet liquid may dissociate from the solid, and independently form a liquid droplet in the external environment. If the three-phase contact angle of the droplet liquid component is less than 1° on the internal solid material within a volume of external liquid material, then liquid remains around the internal solid material rather than dissociating from it.

Figure 2A:
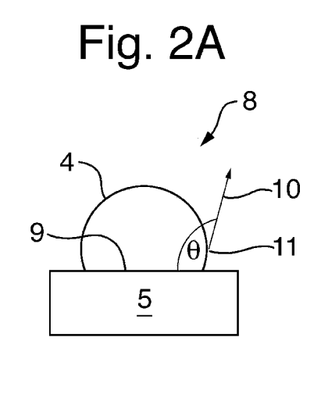
Figure 2B:
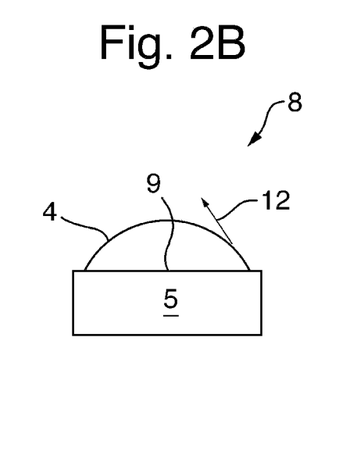
Figure 2C:
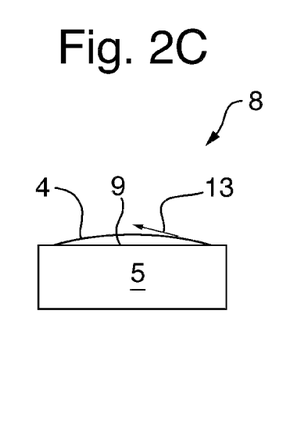

FIG. 2A, FIG. 2B, and FIG. 2C represent the steps in measuring the three-phase contact angle. The three-phase contact angle is measured by placing a sample of the internal solid material (5) into a sample of external liquid material (8). Next a droplet of a second liquid (4) which is immiscible with the external liquid material (i.e. droplet liquid) is placed on the solid surface (9). The contact angle (10) is then measured as a tangent from the internal solid material surface (9) along the edge of the droplet (11), as shown in FIG. 2A. Increasing 'wettability' of the internal solid material by the droplet liquid material leads to a decreasing contact angle (12) (FIG. 2B) until total wetting is seen at very low angles (13) (FIG. 2C). Increased wetting means that the droplet liquid material preferably remains associated with the internal solid material rather than dissociating from it. The method for determining the three-phase contact angle is described in more detail below.

The liquid droplet may have a volume of 1 ml or less. By 'volume' we herein mean the space occupied by the liquid droplet. The liquid droplet may have a volume of 0.8 ml or less, or even 0.6 ml or less. The liquid droplet may have a volume of at least 0.5 picoliters, or even 4 picoliters, or even 35 picoliters.

The liquid droplet may have at least one orientation having a circularity of less than 0.9, or even less than 0.8, or even less than 0.7. "Orientation" as used herein means the two-dimensional projected area of a three-dimensional shape when viewed from any given point. A three-dimensional shape will present different orientations depending upon the angle or point from which it is viewed. Thus, at least one of these orientations must have a circularity of less than 0.9. This means that from a different orientation, or orientations, the same liquid droplet may have a circularity of greater than 0.9. The circularity may be at least 0.1, or even 0.2, or even 0.3. Without wishing to be bound by theory, a perfect circle has a circularity of 1.0 Circularity is a non-unit value of the two-dimensional projected area of a particle multiplied by $4\pi$, and then divided by the square of the projected perimeter of the particle;

$$\text{Circularity} = \frac{4\pi * \text{Area}}{\text{Perimeter}^2}$$

Here the projected area is taken to mean the area of a two-dimensional projection of a three-dimensional object onto a flat plane such as an image provided when viewing a microscope slide where a 3D object is placed upon the slide, or a 3D object is sandwiched between a slide and a coverslip. Those skilled in the art would know how to determine the circularity of the projection using standard equipment and techniques known in the art. An exemplary test method is detailed below.

The liquid droplet may have at least one orientation having an aspect ratio of greater than 1.0, or even greater than or equal to 1.5 or even greater than or equal to 2.0, or even greater than or equal to 10 or even greater than or equal to 100. The aspect ratio may be no greater than 200, or even no greater than 175, or even no greater than 150. By "orientation" is meant the two-dimensional projected area of a three-dimensional shape when viewed from any given point. A three-dimensional shape will present different orientations depending upon the angle or point from which it is viewed. Thus, at least one of these orientations must have an aspect ratio of at least 1.0. This means that from a different orientation, or orientations, the same liquid droplet may have an aspect ratio of 1 or less. The aspect ratio is determined by assigning a major and minor axis to the projection of the liquid droplet. Here the projected area is taken to mean the area of a two-dimensional projection of a three-dimensional object onto a flat plane such as a microscope slide. This is achieved by fitting an artificial bounding rectangle to the projection of the liquid droplet, where the rectangle dimensions determine each axis value. The aspect ratio is then determined as the ratio of length of the major to minor axis. An exemplary method of determining the aspect ratio is described in more detail below.

Other Droplets

In one embodiment, the spherical or non-spherical liquid droplet may comprise a liquid; and an internal solid material, the internal solid material defining the shape of the droplet; and wherein the liquid or the internal solid material, or both comprise a benefit agent; and wherein the three-phase contact angle of the liquid on the internal solid material is less than about 1°; and wherein, the liquid droplet has a yield stress of between about 100 Pascal and about 100,000 Pascal, when measured at about 25° C.; and wherein, the liquid and the internal solid material are chemically distinct from one another. By "chemically distinct" is meant that the liquid and the internal solid material have different chemistries, for example different chemical species or compounds.

In one aspect, the non-spherical liquid droplet could be a liquid droplet comprising a liquid; and an internal solid material, the internal solid material defining the shape of the droplet; and wherein the three-phase contact angle of the liquid on the internal solid material is less than about 1°; and wherein the liquid droplet has a yield stress of between about 100 Pascal and about 1,000,000 Pascal, when measured at about 25° C.; and wherein the droplet comprises at least 10 weight percent inorganic material; and wherein the droplet comprises at least 1 weight percent of a benefit agent.

The droplet may comprise from 20, or even 30, or even 40, or even 50, or even 60, or even 70, or even 80, or even 90, or even up to 100 weight percent inorganic material.

The droplet may comprise from 5, or even 10, or even 20, or even 30, or even 40, or even 50, or even 60, or even 70, or even 80, or even 90, or even up to 100 weight percent benefit agent.

The liquid may comprise inorganic material. Alternatively the internal solid material may comprise inorganic material. Alternatively, both the droplet liquid and the internal solid material may comprise inorganic material. When present in both, the weight percent of inorganic material comprising the liquid and the solid internal material may be the same or may differ.

The droplet may comprise various materials comprising in part or whole the droplet's liquid and internal solid material. One or more of the materials comprising the liquid may be comprised of one or more benefit agents comprising up to 100 weight percent of the liquid of the droplet. One or more of the materials comprising the internal solid may be comprised of one or more benefit agents comprising up to 100 weight percent of the liquid of the droplet.

The inorganic material may comprise inorganic polymers.

By "inorganic materials" it is meant all substances except hydrocarbons and their derivatives, or all substances that are not compounds of carbon, with the exception of carbon oxides, and carbon sulfide. Suitable inorganic materials may include calcium and zinc salts, zinc oxide, zinc pyrithione calcium-based compounds, bismuth compounds, clays, water, or mixtures thereof. Suitable calcium-based compounds include calcium carbonate. Suitable clays can include laponites, kaolinitie, montmorillonite, atapulgite, illite, bentonite, halloysite and mixtures thereof. Inorganic polymers are polymers in which the main chain contains no carbon atoms. Suitable inorganic polymers include polysilanes, polygermanes, polystannanes, polysulfides; and heterochain polymers with more than one type of atom in the main chain such as polyborazylenes, polysiloxanes like polydimethylsiloxane (PDMS), polymethylhydrosiloxane (PMHS) and polydiphenylsiloxane, polysilazanes like perhydridopolysilazane (PHPS), polyphosphazenes, polythiazyls and mixtures thereof.

In one embodiment, the non-spherical liquid droplet may comprise a liquid; and an internal solid material, the internal solid material defining the shape of the droplet; and wherein the three-phase contact angle of the liquid on the internal solid material is less than about 1°; and wherein the liquid droplet has a yield stress of between about 100 Pascal and about 1,000,000 Pascal, when measured at about 25° C.; and wherein the droplet comprises at least 10 weight percent in total from the group of organo-compounds, synthetic organic polymers, and semisynthetic organic polymers; and wherein the droplet comprises at least 1 weight percent of a benefit agent.

The droplet may comprise from 20, or even 30, or even 40, or even 50, or even 60, or even 70, or even 80, or even 90, or even up to 100 weight percent organo-compounds, synthetic organic polymers, semisynthetic organic polymers, or mixtures thereof.

The droplet may comprise from 5, or even 10, or even 20, or even 30, or even 40, or even 50, or even 60, or even 70, or even 80, or even 90, or even up to 100 weight percent benefit agent.

The droplet liquid may comprise from 5, or even 10, or even 20, or even 30, or even 40, or even 50, or even 60, or even 70, or even 80, or even 90, or even up to 100 weight percent benefit agent.

The droplet liquid, the internal solid material or a combination thereof may comprise organo-compounds, synthetic organic polymers, semisynthetic organic polymers, or a mixture thereof.

The droplet may comprise at least 1, or even 2, or even 5, or even 10, or even 20, or even 30, or even 40, or even 50, or even 60, or even 70, or even 80, or even 90, or even 100 weight percent organo-compound material. The droplet may comprise at least 1, or even 2, or even 3, or even 4, or even 5, or even 10, or even 20, or even 30, or even 40, or even 50, or even 60, or even 70, or even 80, or even 90, or even 100 weight percent of a benefit agent. Organo-compound material is an organic compound to which one or more non-oxygen hetero-atoms replace one or more carbon atoms in a hydrocarbon chain of an organic material and/or acts in the stead of a carbon atom in an otherwise hydrocarbon chain of an organic material. Example organo compounds, including polymeric forms, include: thio-compounds (also known as sulfur-containing organo compounds such as thiols, sulfides, and disulfides); phosphorous-containing compounds (such as phosphines and phosphoniums); nitrogen-containing compounds (such as amines and ammonium); organosilicon compounds (such as silanes, silyl halides, silanols, siloxanes, alkoxysilanes, silizanes, and polydimethylsiloxane); organoboron compounds (such as boranes); organometallic compounds; organoclay (also known as organopolysilicate) compounds such as kaolin or montmorillonite to which an organic structure has been chemically bonded; organotin compounds; organozinc compounds; and mixtures thereof. The organo-compound material may be comprised of one or more organo compounds.

The droplet may comprise at least 1, or even 2, or even 5, or even 10, or even 20, or even 30, or even 40, or even 50, or even 60, or even 70, or even 80, or even 90, or even 100 weight percent of a synthetic organic polymer or a semisynthetic organic polymer. Semisynthetic involves additional actions beyond hydrogenating a natural polymer to increase its degree of saturation.

Synthetic organic polymer materials include thermoplastics such as Acrylonitrile butadiene styrene (ABS), Acrylic, Celluloid, Cellulose acetate, Ethylene-Vinyl Acetate (EVA), Ethylene vinyl alcohol (EVAL), Fluoroplastics (PTFEs, including FEP, PFA, CTFE, ECTFE, ETFE), Ionomers, acrylic/PVC alloy (such as Kydex, a trademarked product), Liquid Crystal Polymer (LCP), Polyacetal (POM or Acetal), Polyacrylates (Acrylic), Polyacrylonitrile (PAN or Acrylonitrile), Polyamide (PA or Nylon), Polyamide-imide (PAI), Polyaryletherketone (PAEK or Ketone), Polybutadiene (PBD), Polybutylene (PB), Polybutylene terephthalate (PBT), Polyethylene terephthalate (PET), Polycyclohexylene dimethylene terephthalate (PCT), Polycarbonate (PC), Polyhydroxyalkanoates (PHAs), Polyketone (PK), Polyester, Polyethylene (PE) including low density (LDPE) and high density (HDPE) versions, Polyetheretherketone (PEEK), Polyetherimide (PEI), Polyethersulfone (PES), Polysulfone, Polyethylenechlorinates (PEC), Polyimide (PI), Polylactic acid (PLA), Polymethylpentene (PMP), Polyphenylene oxide (PPO), Polyphenylene sulfide (PPS), Polyphthalamide (PPA), Polypropylene (PP), Polystyrene (PS), Polysulfone (PSU), Polyvinyl chloride (PVC), Polyvinylidene chloride (PVDC), Fluoropolymer (e.g., Spectralon), or mixtures thereof. Semisynthetic organic polymer materials include cross-linked thermosets such as those involving epoxy, phenol formaldehyde, urea formaldehyde, phenolics, alkyds, amino resins, polyesters, epoxides, silicones, proteins; other cross-linked materials such as natural and synthetic rubbers (which may be cured, for example, via vulcanization); and mixtures thereof. Semisynthetic organic polymer materials include cellulosics (such as cellulose gum, cellulose triacetate, nitrocellulose, rayon, cellophane and other modified celluloses), and modified starches (including those that have been physically treated, enzymatically treated, or chemically treated, such as by acetylation, chlorinations and acid hydrolysis), and mixtures thereof.

In one aspect, the non-spherical liquid droplet comprises a liquid; and an internal solid material, the internal solid material defining the shape of the droplet; and wherein the three-phase contact angle of the liquid on the internal solid material is less than about 1°; and wherein the liquid droplet has a yield stress of between about 100 Pascal and about 1,000,000 Pascal, when measured at about 25° C.; and wherein the droplet comprises less than 95 weight percent lipid material; and wherein the droplet comprises at least 1 weight percent of a benefit agent.

The droplet may comprise less than 80, or even less than 70, or even less than 60, or even less than 50, or even less than 40, or even less than 30 weight percent lipid material.

The droplet may comprise from 5, or even 10, or even 20, or even 30, or even 40, or even 50, or even 60, or even 70, or even 80, or even 90, or even up to 100 weight percent benefit agent.

The droplet liquid may comprise from 5, or even 10, or even 20, or even 30, or even 40, or even 50, or even 60, or even 70, or even 80, or even 90, or even up to 100 weight percent benefit agent.

In one embodiment the non-spherical liquid droplet comprises a liquid; and an internal solid material, the internal solid material defining the shape of the droplet; and wherein the three-phase contact angle of the liquid on the internal solid material is less than about 1°; and wherein the liquid droplet has a yield stress of between about 100 Pascal and about 1,000,000 Pascal, when measured at about 25° C.; and wherein the droplet comprises less than 95 weight percent total hydrocarbons; and wherein the droplet comprises at least 1 weight percent of a benefit agent.

The droplet may comprise less than 80, or even less than 70, or even less than 60, or even less than 50, or even less than 40, or even less than 30 weight percent hydrocarbon material.

The droplet may comprise from 5, or even 10, or even 20, or even 30, or even 40, or even 50, or even 60, or even 70, or even 80, or even 90, or even up to 100 weight percent benefit agent.

The droplet liquid may comprise from 5, or even 10, or even 20, or even 30, or even 40, or even 50, or even 60, or even 70, or even 80, or even 90, or even up to 100 weight percent benefit agent.

Lipids constitute a broad group of naturally occurring molecules that include fats, waxes, sterols, fat-soluble vitamins (such as vitamins A, D, E, and K), monoglycerides, diglycerides, triglycerides, phospholipids, and others. Lipids may be derived from an organism such as animal, fungus, micro-organism, or plant. The droplet may comprise at least 1, or even 2, or even 3, or even 4, or even 5, or even 10, or even 20, or even 30, or even 40, or even 50, or even 60, or even 70, or even 80, or even 90, or even 100 weight percent of a benefit agent.

The droplet may comprise up to 95 weight percent lipid material. The droplet may comprise less than 1, or even 2, or even 5, or even 10, or even 20, or even 30, or even 40, or even 50, or even 60, or even 70, or even 80, or even 90 weight percent lipid. The total weight of the lipid of the droplet can be wholly comprised within the liquid or the internal solid material, or may be apportioned between the liquid and the internal solid material in respective ratios, which add up to no greater than 100%, of: more than or equal to 10% and less than or equal to 90%, more than or equal to 20% and less than or equal to 80%, more than or equal to 30% and less than or equal to 70%, more than or equal to 40% and less than or equal to 60%, more than or equal to 50% and less than or equal to 50%, more than or equal to 60% and less than or equal to 40%, more than or equal to 70% and less than or equal to 30%, more than or equal to 80% and less than or equal to 20%, and more than or equal to 90% and less than or equal to 10%. In another example, the droplet may comprise a liquid that is 100% lipid and an internal solid material that is comprised of less than 100%, less than 90%, less than 80%, less than 70%, less than 60%, less than 50%, less than 40%, less than 30%, less than 20%, less than 10% lipid or contain no lipid. In another example, the internal solid material may comprise a liquid that is 100% lipid and a droplet that is comprised of less than 100%, less than 90%, less than 80%, less than 70%, less than 60%, less than 50%, less than 40%, less than 30%, less than 20%, less than 10% lipid or contain no lipid.

The remainder of the droplet may comprise non-lipid material, such as inorganic polymers; hydrocarbons; organo-compound materials; synthetic organic polymers; semisynthetic organic polymers; alkyl halides; peroxides; carbohydrates including sugars, simple starches, polysaccharides (such as starches, cellulose), pectins, gums (such as gellan and xanthan), or mixtures thereof. The droplet may also comprise non-lipidic materials such as aliphatic compounds (including paraffin, also known as alkane compounds), olefinic compounds, and acetylenic compounds; cyclic compounds which include alicyclic compounds, aromatic hydrocarbon compounds, and heterocyclic compounds including pyroles, furans, and thiazoles; alcohols including fatty alcohols; ethers; aldehydes and ketones or mixtures thereof.

Hydrocarbons are organic compounds consisting exclusively of the elements carbon and hydrogen. Hydrocarbons may be derived from oil, petroleum, coal, or natural gas. The droplet may comprise up to 95 weight percent hydrocarbon material. The droplet may comprise at least 1, or even 2, or even 3, or even 4, or even 5, or even 10, or even 20, or even 30, or even 40, or even 50, or even 60, or even 70, or even 80, or even 90, or even 100 weight percent of a benefit agent. The droplet may comprise less than 1, or even 2, or even 5, or even 10, or even 20, or even 30, or even 40, or even 50, or even 60, or even 70, or even 80, or even 90 weight percent hydrocarbon. The total weight of the hydrocarbon of the droplet can be wholly comprised with the liquid or the internal solid material, or may be apportioned between the liquid and the internal solid material in respective ratios, which add up to no greater than 100%, of: more than or equal to 10% and less than or equal to 90%, more than or equal to 20% and less than or equal to 80%, more than or equal to 30% and less than or equal to 70%, more than or equal to 40% and less than or equal to 60%, more than or equal to 50% and less than or equal to 50%, more than or equal to 60% and less than or equal to 40%, more than or equal to 70% and less than or equal to 30%, more than or equal to 80% and less than or equal to 20%, and more than or equal to 90% and less than or equal to 10%.

The hydrocarbon may comprise aliphatic compounds such as paraffin (also known as alkane compounds); olefinic compounds; acetylenic compounds; and alicyclic and aromatic hydrocarbon compounds. The remainder of the droplet may comprise non-hydrocarbon material. Said non-hydrocarbon material may comprise material including inorganic polymers; lipids; organo-compound materials; non-hydrocarbon synthetic organic polymers; non-hydrocarbon semisynthetic organic polymers; alkyl halides; peroxides; carbohydrates including sugars, simple starches, polysaccharides (such as starches, cellulose); pectins; gums (like gellan and xanthan); or mixtures thereof; heterocyclic compounds (such as pyroles, furans, and thiazoles); alcohols (such as fatty alcohols); ethers; aldehydes; ketones; and mixtures thereof.

It is noted that some organic compounds can be considered to fall into multiple groups or classes (e.g. ethers and amines). Organic compounds may be derived from living organisms such as animal, fungus, micro-organism, or plant, or from non-renewable resources such as oil, petroleum, coal, or natural gas. Organic compounds may be extracted directly from the source, possibly with purification, separation, distillation, or other process steps. Organic compounds may be synthesized or prepared by one or more chemical steps, such as by reaction, possibly involving multiple starting compounds. For example, polymers are produced from monomers during a polymerization step. Synthetic polymers may be formed by using a combination of monomers derived from renewable resources such as recently living plant or animal sources; and, monomers derived from non-renewable resources such as coal, petroleum, oil, and natural gas.

Liquid

The liquid droplet comprises a liquid (also referred to as the "droplet liquid"). The liquid can be any suitable liquid that exhibits a three-phase contact angle with the internal solid material of less than 1°. The liquid may be an aqueous liquid or an oil or an alcohol.

The droplet liquid may be an oil, even a hydrophobic oil. The oil may have a melting point of greater than 10° C., or even 5° C. or even −20° C. The oil may have a melting point no greater than 25° C., or even no greater than 22.5° C., or even no greater than 20° C.

The oil may be selected from alkanes, tri- and di- and monoglycerides, saturated and unsaturated fatty acids, sterols, silicone oils, fluorinated oils, mineral oils, and mixtures thereof. Oils may be sourced from petroleum, vegetable, animal, fish or plant materials. Oils can be derived from natural oil-containing materials, or can be synthetically produced.

The droplet liquid may also be an aqueous liquid. The aqueous liquid may be an aqueous solution of surfactant, an aqueous dispersion of colloidal particles, an aqueous solution of polymer, or mixtures thereof. Suitable surfactants can include anionic, non-ionic, cationic, zwitterionic, or a mixture thereof.

The droplet liquid may also be an alcohol. Suitable alcohols may include alcohols such as ethanol, propanol, butanol, pentanol, hexanol, and octanol. It should be noted that both the liquid and the internal solid material may comprise fatty alcohols. Suitable alcohols may also include fatty alcohols. Fatty alcohols (such as stearyl alcohol) making up the internal material may be distinguished from fatty alcohols in the liquid by the fact that the fatty alcohol making up the internal solid material has a melting point no lower than 40° C. while the fatty alcohol present in the droplet liquid has a melting point of greater than 10° C., or even 5° C. or even −20° C., but no greater than 25° C., or even no greater than 22.5° C., or even no greater than 20° C.

Internal Solid Material

The internal solid material may have a yield stress of at least 10,000 Pascals, or even at least 12,500 Pascals, or even at least 15,000 Pascals. The internal solid material may have a yield stress of at most 100,000,000,000 Pascals, or even 10,000,000,000 Pascals, or even 1,000,000,000 Pascals, or even 100,000,000 Pascals, or even 10,000,000 Pascals, or even 1,000,000 Pascals. The yield stress of the internal solid material is measured at a temperature of 25° C.

The internal solid material may be porous or non-porous and may be water-soluble or water-insoluble.

Figure 3:
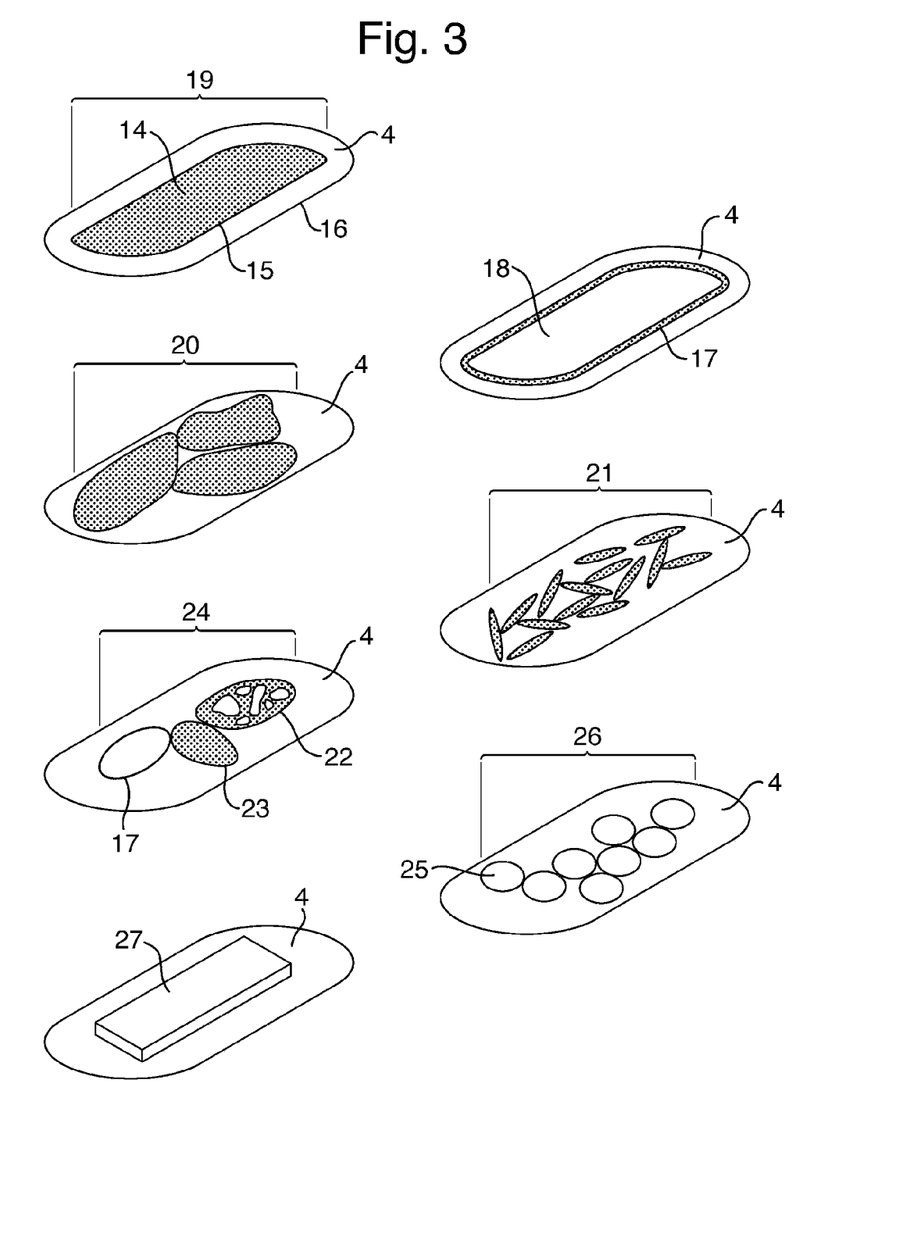

FIG. 3 discloses non-limiting examples of the non-spherical droplets of the present invention. The internal solid material may be porous. By "porous" is meant a solid material which comprises a void volume within the solid material. The void volume may comprise the droplet liquid, or may be completely devoid of the droplet liquid. The void volume may comprise the benefit agent. The droplet liquid (4) completely surrounds the internal solid material (14) and the distance between any point on the surface of the internal solid material (15) and the outer surface of the droplet (16) can vary from another point on the surface of the internal solid material and the outer surface of the droplet, i.e. the 'thickness' of the liquid part of the liquid droplet may vary. Alternatively the internal solid material may be non-porous. The internal solid material may be in the form of a shell (17) in which there exists a chamber (18) within the solid material. This chamber (18) may contain another material. The internal solid material may exist as a single structure, for example a single solid structure (19) within the liquid droplet or may exist as more than one structure (20). If there is more than one structure, these structures may or may not be in contact with one another within the liquid droplet. The internal solid material could be an assembly of discrete components. For example, this assembly could be comprised of a series of rod shaped solid materials (21) which are in close contact but which comprise a void volume between each other. In this instance, the internal solid material will be porous due to the void volume existing between the rod shape solid materials. Alternatively, the internal solid material may comprise a porous material (22), non-porous material (23) in which there exists no void volume, shell material (17) or a combination thereof (24).

The internal solid material may comprise an assembly of solid forms or components which in their positioning make up the overall internal shape, whether it be for example a rod or a ring-like overall shape. In one example, the shape of the internal solid material may be rod shaped, or be an assembly of rods or splines or needles that give an overall rod shape to the liquid droplet. The internal solid material in a rod shape may be porous, non-porous, be a shell, or be a tube/pipe (i.e. hollow within and open at both ends). An assembly of rods may comprise porous rods, non-porous rods, rod shaped shells, tubes/pipes, or mixtures thereof. Alternatively, the internal solid material may be comprised of spherically shaped forms or subcomponents (25), in which case the internal solid material would need to be an assembly of spherical shapes (26) which in their totality give the liquid droplet a non-spherical shape. Alternatively, the internal solid material may have a substantially flat profile (27) (i.e., comprises at least two sides that are substantially planar).

The solid material may be selected from waxes, polymeric materials, fatty materials, inorganic materials or mixtures thereof. Waxes may be sourced from petroleum, vegetable, animal, fish or plant materials. Waxes can be derived from natural wax-containing materials or may be synthetically produced.

Suitable waxes can include synthetic waxes, mineral waxes, hydrocarbon waxes, plant waxes, animal waxes, or mixtures thereof. Synthetic waxes can comprise polyethylene. Mineral waxes can include ozokerite. Hydrocarbon waxes can comprise paraffins, microcrystalline hydrocarbon waxes, petrolatum waxes, or mixtures thereof. Plant waxes can comprise castor wax, carnauba wax, or mixtures thereof. Animal waxes can comprise beeswax, spermaceti or mixtures thereof. Other suitable waxes can include those commercially available under the trade names Castrolatum™, Super White Proto-Pet™, Thixcin-R™, or mixtures thereof.

Suitable polymeric materials can include cellulose, polydimethylsiloxane, polymethylmethacrylate, polyethylene oxide, biopolymers, or mixtures thereof. Suitable biopolymers can include gums such as gellan, xanthan, and carrageenan or mixtures thereof. Other polymers include polysiloxanes, polyamides, polyamines, polycarbonates, and polyesters.

Suitable fatty materials may comprise tri- and di- and monoglycerides, saturated and unsaturated fatty acids, sterols, and fatty alcohols. Fatty alcohols (such as stearyl alcohol) making up the internal material may be distinguished from fatty alcohols in the liquid by the fact that the fatty alcohol making up the internal solid material has a melting point no lower than 40° C. Suitable alcohols for the internal solid include cetyl alcohol, stearyl alcohol, and behenyl alcohol.

Suitable inorganic materials may include zinc oxide, zinc pyrithione calcium-based compounds, bismuth compounds, clays, or mixtures thereof. Suitable calcium-based compounds include calcium carbonate. Suitable clays include laponites, kaolinitie, montmorillonite, atapulgite, illite, bentonite, halloysite, and mixtures thereof.

Benefit Agent

The liquid droplet comprises a benefit agent. The liquid droplet may comprise from 0.0001%, or even from 0.1%, or even from 1% to 50%, or even to 40%, or even to 30%, or even to 20% by weight of the benefit agent.

The benefit agent may be a liquid or a solid. If the benefit agent is solid, then it must have a three-phase contact angle of the droplet liquid on the solid benefit agent of less than 1°. If the benefit agent is liquid, then if present in the droplet liquid, the droplet liquid/benefit agent mixture must have a three-phase contact angle on the internal solid material of less than 1°. If the benefit agent is liquid, then if present in the internal solid material, there must be a three-phase contact angle of the droplet liquid on the internal solid material/liquid benefit agent mixture of less than 1°. The internal solid material/liquid benefit agent mixture can have a yield stress of at least 10,000 Pascals, or even at least 12,500 Pascals, or even at least 15,000 Pascals, and preferably a yield stress of at most 100,000,000,000 Pascals, or even 10,000,000,000 Pascals, or even 1,000,000,000 Pascals, or even 100,000,000 Pascals, or even 10,000,000 Pascals, or even 1,000,000 Pascals. The yield stress is measured at a temperature of 25° C. Alternatively, a solid benefit agent may be dissolved in a liquid, wherein the mixture comprising the liquid and dissolved solid benefit agent has a three-phase contact angle with the internal solid material of less than 1°.

The benefit agent may be fully or partly enclosed within the internal solid material or may be attached to the solid material. Alternatively, it may be present within the droplet liquid, or it may be present in both the liquid and the internal solid material.

The benefit agent may be selected from compounds useful in cleaning compositions, such as fabric or household cleaning compositions, body wash and body care compositions, hair and beauty care compositions, health care compositions, or mixtures thereof.

The benefit agent may be a surfactant. Suitable surfactants can be selected from anionic, non-ionic, zwitterionic, cationic, or mixtures thereof. If the benefit agent is a surfactant and the liquid present in the liquid droplet comprises a surfactant then the two surfactants must be different. Suitable surfactants can include lipids of biological origin such as fatty acids, acyl glycerols, glycerolphospholipids, phosphatidic acid (and salts thereof), phosphatidylethanolamine, phosphatidylcholine (lecithin), phosphatidylserine, phosphatidyllinositol, phosphatidylethanolamine, sphingolipids (e.g., ceramides), sphingomyelin, cerebroside, glucocerebroside, ganglioside, steriods, cholesterol esters (e.g., stearates), sugar-based surfactants, glucolipids, galactolipids, and combinations thereof.

The benefit agent may be transition metal catalysts; imine bleach boosters; enzymes such as amylases, carbohydrases, cellulases, laccases, lipases, bleaching enzymes such as oxidases and peroxidases, proteases, pectate lyases and mannanases; sources of peroxygen; bleach activators such as tetraacetyl ethylene diamine, oxybenzene sulphonate bleach activators such as nonanoyl oxybenzene sulphonate, caprolactam bleach activators, imide bleach activators such as N-nonanoyl-N-methyl acetamide, preformed peracids such as N,N-pthaloylamino peroxycaproic acid, nonylamido peroxyadipic acid or dibenzoyl peroxide; suds suppressing systems such as silicone based suds suppressors; brighteners; hueing agents; photobleach; fabric-softening agents such as clay, silicone, and/or quaternary ammonium compounds; flocculants such as polyethylene oxide; dye transfer inhibitors such as polyvinylpyrrolidone, poly 4-vinylpyridine N-oxide and/or co-polymer of vinylpyrrolidone, and vinylimidazole; fabric integrity components such as oligomers produced by the condensation of imidazole and epichlorhydrin; soil dispersants and soil anti-redeposition aids such as alkoxylated polyamines and ethoxylated ethyleneimine polymers; anti-redeposition components such as polyesters and/or terephthalate polymers, polyethylene glycols including polyethylene glycol substituted with vinyl alcohol and/or vinyl acetate pendant groups; perfumes; cellulosic polymers such as methyl cellulose, carboxymethyl cellulose, hydroxyethoxycellulose, or other alkyl or alkylalkoxy cellulose, and hydrophobically modified cellulose; carboxylic acid and/or salts thereof, including citric acid and/or sodium citrate; and any combination thereof.

A benefit agent can comprise perfumes, brighteners, insect repellants, silicones, waxes, flavors, vitamins, fabric softening agents, and/or skin care agents. Suitable benefit agents include silicones, enzymes, fragrances, perfumes, perfume raw materials, fragrance raw materials, deodorants, odor counteractants, malodors, essential oils, ethers, esters, ketones, alcohols, glycols, silicone hydrocarbons, cyclic hydrocarbons, aldehydes, terpines, volatile insecticides, volatile insect repellants, volatile pesticides, volatile antimicrobial agents, volatile fungicides, volatile herbicides and mixtures thereof. Skin benefit agents suitable for use in the present invention may include salicylic acid, Vitamin C, Vitamin E, Vitamin A, alpha hydroxy acids, glycolic acids, N-6 furfuryladenine, ethyl resorcinol, niacinamide, zinc pyrithione, selenium sulphide, octopirox, ketoconazole, climbazole and salicylic acid. Finasteride, protease inhibitors connected with hair growth regulation, keratinization regulators (e.g., zinc pyrithione (ZPT), tar based compositions, steroids (e.g. corticosteroids), selenium sulfide, imidazole, ketoconazole, hydroxypyridones, and naturopathic agents); octopirox, climbazole, trichogen; climbazole and zinc gluconate.

Oftentimes, benefit agents are expensive, therefore improved delivery, such as by the droplet of this invention, can help make effective use of such components.

Composition Comprising the Liquid Droplet

One aspect of the present invention is a composition comprising an external liquid and the liquid droplet according to the present invention. The liquid droplet and the external liquid are immiscible with one other. The composition can be, for example, a fully formulated consumer goods product, for example a liquid detergent, shampoo, or a liquid hand soap. Alternatively the composition could be a liquor prepared by the consumer, for example a fabric or dish wash liquor. The composition can be a fabric care, home care, health care, or beauty care product; a medicament; or a nutraceutical composition.

The liquid droplet is within the external liquid. The liquid droplet is immiscible with the external liquid. The external liquid can be a hydrophilic liquid such as an aqueous liquid, or an oleophilic liquid such as an oil. If the external liquid is an aqueous liquid, then the droplet liquid is an oil. Alternatively, if the external liquid is an oil, then the droplet liquid is an aqueous liquid.

Suitable external liquids can include water, aqueous liquid comprising a surfactant, an aqueous dispersion of colloidal particles, an aqueous solution of polymer, or mixtures thereof.

The composition may also comprise adjunct materials other than the liquid droplets. Adjunct ingredients can include those that are commonly found in fabric, home, beauty, or health care compositions. Those skilled in the art would recognize such suitable adjunct ingredients.

Method of Depositing Benefit Agent on a Substrate

The present invention also contemplates a method of depositing a benefit agent on a substrate comprising the steps of;
  i) preparing a non-spherical liquid droplet, wherein the liquid droplet comprises;
    a) a liquid;
    b) an internal solid material, the internal solid material defining the shape of the droplet; and
    c) a benefit agent;
    wherein the three-phase contact angle of the liquid on the internal solid material is less than 1°;
    and wherein the droplet has a yield stress of between 100 Pascal and 1,000,000 Pascal, or even between 1000 Pascal and 100,000 Pascal; and
  ii) contacting the liquid droplet with the substrate.

The liquid droplet may be in the form of an aerosol, i.e. a liquid dispersion in air. Alternatively, the liquid droplet may be in an external liquid, wherein the liquid droplet is immiscible in the external liquid.

The liquid droplet may be the liquid droplet according to the present invention. The liquid, internal solid material, benefit agent, three-phase contact angle, yield stress and external liquid are as described above.

Method of Making a Non-Spherical Droplet

Another aspect of the present invention is a method for making the non-spherical liquid droplets of the present invention comprising the steps of;
  i) mixing a first liquid composition comprising a molten ingredient having a yield stress of between 100 and 1,000,000 Pascals, the yield stress being measured at a temperature of 25° C., and a second liquid and a benefit agent, wherein the first and second liquids and benefit agent are mixed at a temperature above 50° C. to make a liquid droplet premix;
  ii) preparing a channel, wherein the channel optionally comprises a third liquid, the third liquid being immiscible with the second liquid, and wherein the third liquid flows through the channel;
  iii) drawing individual droplets of the liquid droplet premix into the channel, wherein the channel comprises a constriction to shape the droplet;
  iv) passing the premix droplets into the constriction at a temperature of 50° C. or below so that the first liquid solidifies to produce liquid non-spherical droplets;
  v) depositing the non-spherical liquid droplets into a composition comprising the third liquid, the third liquid being immiscible with the second liquid.

The liquid droplet premix comprises two separate fractions. The first fraction corresponds to the internal solid material in a molten state and the second fraction corresponds to the droplet liquid and the benefit agent. In order to shape the non-spherical liquid droplet, these three components exist in the droplet premix as a homogenous mixture at a temperature above 50° C. The benefit agent may be a liquid or a solid. If the benefit agent is solid, then it must have a three-phase contact angle of the liquid on the solid benefit agent of less than 1°. If the benefit agent is liquid, then when dissolved in the droplet liquid, the droplet liquid/benefit agent mixture must have a three-phase contact angle on the internal solid material of less than 1°. Alternatively, a solid benefit agent may be dissolved in a liquid, wherein the mixture comprising the liquid and dissolved solid benefit agent has a three-phase contact angle with the internal solid material of less than 1°.

In step (iv) above, this homogenous premix is drawn into a constriction to shape the droplet, while simultaneously cooling the mixture to a temperature of 50° C. or less. Suitable means of lowering the temperature could be a heat exchanger, for example a water bath or a cooling jacket. As the temperature is decreased, the first fraction (molten internal solid material) cools and solidifies in a non-spherical shape. Due to the interactive forces between the shaped internal solid material and the liquid, the droplet maintains a non-spherical shape. The interactive forces are explained in more detail above in relation to the three-phase contact angle.

The constriction may be in the form of a capillary, or one in which the droplet premix is extruded through a membrane system or one in which the droplet premix is passed through a fiber-spinning apparatus or a mold, or a mixture thereof.

Figure 4:
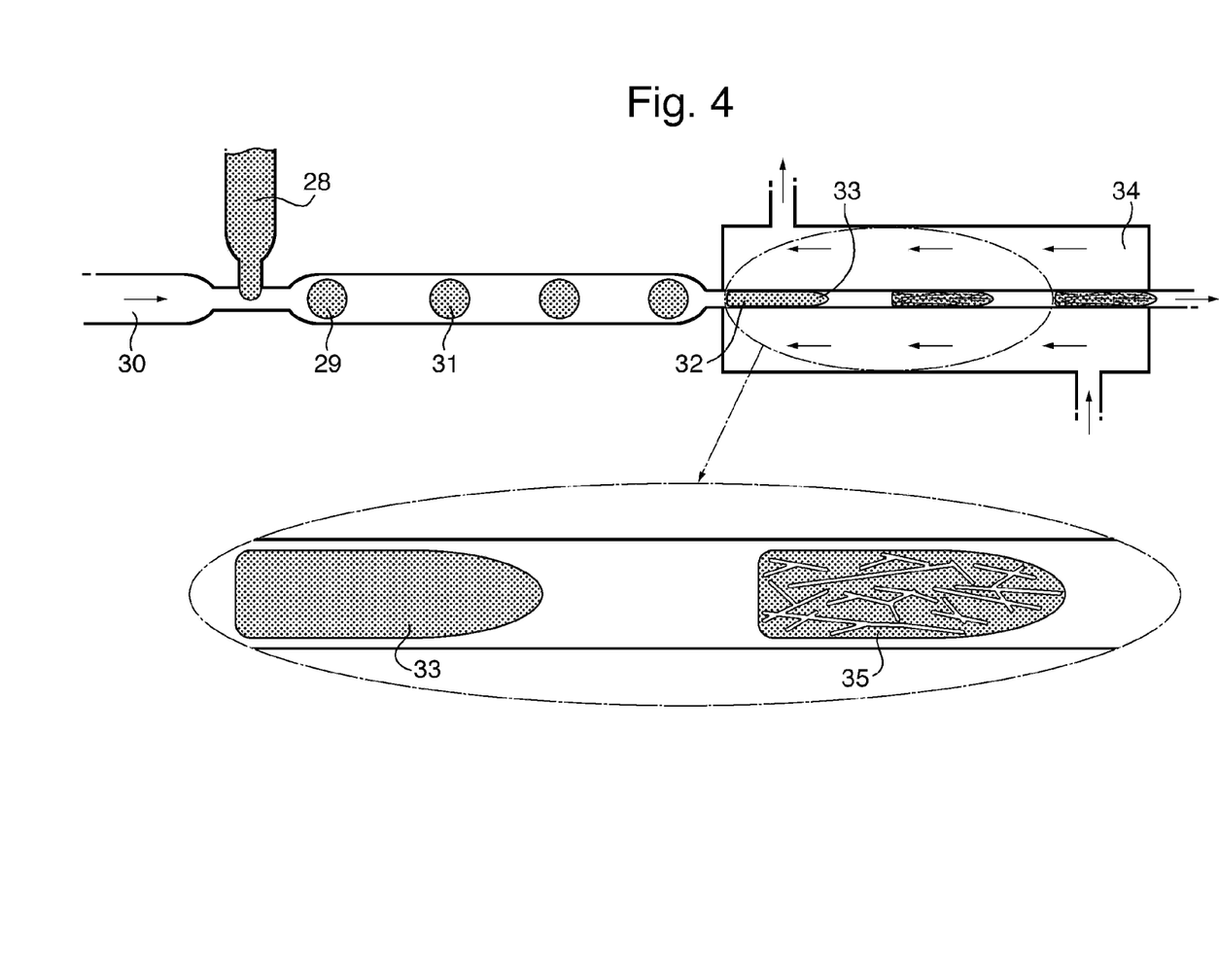

FIG. 4 shows an exemplary means to shape the liquid droplet. The droplet premix (28) is injected into the channel (29) wherein the third liquid (30) is flowing through the channel. Individual droplets of the droplet premix (29) pass into a restricted capillary zone (32) in which the droplet premix is shaped into a non-spherical shape (33). The capillary passes through a heat exchanger to lower the temperature to 50° C. or below (34). As the droplets of the liquid droplet premix pass through the cooling means (34), the internal solid material solidifies (35).

EXAMPLES

Test Methods

Circularity was measured by optical microscopy using a Zeiss Axiscop microscope, fitted with a 20× objective lens, available from Carl Zeiss MicroImaging Inc. in Thornwood, N.Y. A 1 mL sample of a droplet dispersion was placed on a microscope slide and positioned under the objective lens. The sample was viewed through the ocular lenses and the focus and illumination adjusted until the droplets were visually clear. An image of the individual droplet was then digitized using ImageJ image analysis program, available from National Institutes of Health in Bethesda, Md. Using ImageJ software, the digitized image was then analyzed using the area and perimeter analysis options to measure the droplet's two-dimensional area and perimeter. The values reported on the screen were then used to calculate the circularity using the equation given above.

Aspect ratio was measured by image analysis using a Zeiss Axiscop microscope, fitted with a 20× objective lens, available from Carl Zeiss MicroImaging Inc. in Thornwood, N.Y. A 1 mL sample of a droplet dispersion was placed on a microscope slide and positioned under the objective lens. The sample was viewed through the ocular lenses and the focus and illumination adjusted until droplets were visually clear. An image of an individual droplet was then digitized using ImageJ image analysis program, available from National Institutes of Health in Bethesda, Md. Using ImageJ software, the digitized image was then analyzed using the bounding rectangle analysis option. The dimensions of the bounding rectangle were then recorded from the output screen shown and used to calculate the aspect ratio by taking the major axis value and dividing it by the minor axis value.

Yield stress was measured using a TA Instruments AR2000 stress-controlled rheometer available from TA Instruments of New Castle Del., fitted with a 40 mm 2 degree angle cone and plate attachment.

A 0.5 gram sample was placed on the bottom plate and the temperature set to 25° C. For a liquid material the sample was poured onto the plate, while a solid sample was cut into a cylindrical shape having the diameter of the cone and a height of 1 millimeter.

The cone was lowered until the apparatus software determined the position of the sample.

The sample was heated to 60° C. and mixed for 5 minutes at a shear rate of 100 $s^{-1}$.

The sample was then cooled from 60° C. to 25° C. at 5° C. per minute while oscillating the sample with a strain of 0.1% at a frequency of 1 Hertz.

The apparatus measured and recorded the elastic modulus, G', every 10 seconds during the oscillation.

Once 25° C. was reached, G' measurement and recording continued and a gradual increase in strain was conducted until reaching 100%. G' was plotted as a function of strain.

The value of G' will exhibit a constant plateau value at low strain values and the critical strain is defined as the strain at which the G' first drops below its plateau value by 20% or more.

The yield stress is then calculated as the product of the critical strain and the G' plateau value.

For example, a sample that has a G' plateau value of 10,000 Pascals and a critical strain of 0.2% has a yield stress of 20 Pa.

The three-phase contact angle was measured using a Kruss DSA100 droplet shape analyzer that is available from Kruss Instruments of Hamburg Germany.

A flat sample of the solid to be characterized was prepared by cutting it so the surface was flat and not contaminated with dust.

The first liquid to be characterized was then placed on the flat sample of the solid at the bottom of a rectangular quartz cuvette, and the cuvette placed on the sample plate. The cuvette was then filled with the first liquid.

A droplet of the second liquid was then placed on the surface of the solid sample.

The apparatus was then used to measure the contact angle using the contact angle calculation function of the DSA1 software, available from Kruss Instruments of Hamburg Germany, that performs a best-fit of the boundary of the droplet.

The interfacial tension between the droplet and external liquid was measured using a Kruss DSA100 droplet shape analyzer that is available from Kruss Instruments of Hamburg Germany.

A syringe containing the droplet liquid was attached to the syringe holder of the instrument and lowered into a rectangular quartz cuvette containing a sample of the external liquid.

The droplet liquid was then pushed out of the syringe until a droplet formed in the external liquid. The sample was equilibrated for five minutes and then photographed using the interfacial tension function of the DSA1 software that performs a best-fit of the droplet boundary and uses that to calculate the interfacial tension between the two liquids.

Example 1

The following is an example of making a rod shaped droplet. A mixture of 70 wt % Vaseline™ brand petrolatum, 15 wt % Sigma Aldrich light mineral oil, and 15 wt % Shin Etsu silicone oil (benefit agent) was mixed in a beaker. This was heated up while being mixed until completely melted and homogeneous. A 10 millimolar solution of sodium dodecyl sulfate in water was prepared by mixing 2.9 grams of sodium dodecyl sulfate into a liter of water and mixing until a clear solution was formed.

Two Harvard Apparatus PHD 2000 syringe pumps were set to a temperature of 65° C. One syringe pump was filled with the homogenous heated mixture and the other with the sodium dodecyl sulfate composition. The pumps were connected to a Dolomite 3000436 microfluidic chip. IDEX FEP 150 micron ID tubing was connected to the outlet of the chip. The outlet tubing of the chip was surrounded with a concentric copper tube heat exchanger around the microfluidic chip's outlet tubing and its outer tube connected to the reservoir of heat exchanger fluid. The compositions were flowed through the apparatus and rod-shape droplets collected.

Alternatively, the Shin Etsu silicone oil was replaced with 15 wt % Arch Chemicals zinc pyrithione.

Example 2

The following is an example of making a rod shaped droplet. A mixture of 70 wt % Vaseline™ brand petrolatum, 15 wt % Sigma Aldrich light mineral oil, and 15 wt % Shin Etsu silicone oil (benefit agent) was mixed in a beaker. This was heated up while being mixed until completely melted and homogeneous.

IDEX FEP 150 micron ID tubing was connected to the outlet of a New Era Pump Systems metal syringe. The syringe was connected to a syringe pump. An Omega heating tape was wrapped around the syringe and set to a temperature of 61° C. The homogenous mixture was pumped through the apparatus and rod shaped droplets collected in a beaker comprising a 10 millimolar solution of sodium dodecyl sulfate in water. Alternatively, the Shin Etsu silicone oil was replaced with 15 wt % Arch Chemicals zinc pyrithione.

Example 3

Rod-shaped droplets were made as described in Example 1 above. An aqueous composition comprising 1.6 wt % linear alkyl benzene sulfonate, 0.4 wt % of hydrogenated castor oil crystals, 10.07 wt % borax and 0.2 wt % NaOH. The aqueous composition had a yield stress of 1 Pa. To this the rod-shaped liquid droplets were added to a concentration of 1 wt % to make a liquid droplet composition. At a yield stress of 1 Pa, the aqueous composition was such that it prevented aggregation of the liquid droplets (which would give a false positive), yet was not too viscous to pump.

The liquid droplet composition was divided in half and one of the two resulting samples was heated to a temperature above 60° C. for 15 minutes to melt the internal solid material. Upon melting, the rod-shaped droplets assumed a spherical shape (since the interfacial tension is no longer offset by an internal structure).

A volume of 1 ml of the composition being tested was then pushed through a 25 mm Stainless Steel Filter Holder, available from EMD Millipore Corporation in Billerica, Mass., using a 1 mL Becton-Dickinson syringe available from Becton, Dickinson and Company in Franklin Lakes, N.J. The average mesh pore size was ~550 μm. The filter mesh was removed following each test and the entire mesh imaged under a microscope to detect the amount of droplet material that was deposited.

The amount of droplet deposition was measured by optical microscopy using a Zeiss Axioscop microscope, fitted with a 4× objective lens, available from Carl Zeiss Micro-Imaging Inc. in Thornwood, N.Y. The entire filter mesh was placed on a microscope slide and positioned under the objective lens. The sample was viewed through the ocular lenses and the focus and illumination adjusted until the mesh was visually clear. An image of the mesh was then digitized using the ImageJ image analysis program, available from National Institutes of Health in Bethesda, Md.

Using ImageJ software, the digitized image was then analyzed to determine the area of droplets blocking the mesh of the filter using the Measure Particle option with the Area parameter specified as an output. Using the Summary option, the total area of droplets in the filter mesh was determined and compared for each droplet shape.

The average area of filter blockage is reported below for each shape:
Rods: 74.60 square millimeters
Spheres: 1.55 square millimeters As can clearly be seen from the data, a much larger area of the filter mesh was blocked with rod-shaped liquid droplets than spherical liquid droplets. Thus, rod-shaped liquid droplets have much better adhesion to a substrate than spherical liquid droplets.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making a non-spherical droplet, comprising the steps of:

(i) mixing a first liquid composition comprising a molten ingredient comprising a wax or a fatty alcohol, wherein the fatty alcohol has a melting point no lower than 40° C., the molten ingredient having a yield stress of between about 100 and about 100,000 Pascals, the yield stress being measured at a temperature of about 25° C., and a second liquid comprising an oil, water or an alcohol and a liquid benefit agent, wherein the first and second liquids and liquid benefit agent are mixed at a temperature above about 50° C. to make a liquid droplet premix;

(ii) preparing a channel, wherein the channel optionally comprises a third liquid, the third liquid being immiscible with the second liquid, and wherein the third liquid flows through the channel;

(iii) drawing individual droplets of the liquid droplet premix into the channel, wherein the channel comprises a constriction to shape the droplet;

(iv) passing the premix droplets into the constriction at a temperature of about 50° C. or below so that the first liquid solidifies to produce an internal solid material;

(v) forming liquid non-spherical droplets comprising the internal solid material; and (vi) depositing the non-spherical liquid droplets into a composition comprising the third liquid, the third liquid being immiscible with the second liquid.

2. The method according to claim 1, wherein the liquid non-spherical droplet has a yield stress of between about 1000 Pascal and about 100,000 Pascal, when measured at about 25° C.

3. The method according to claim 1, wherein the liquid non-spherical droplet has a volume of about 1 ml or less.

4. The method according to claim 1, wherein the internal solid material comprises at least about 5%, but no more than about 95%, by volume of the liquid non-spherical droplet.

5. The method according to claim 4, wherein the internal solid material comprises at least about 10%, but no more than about 95%, by volume of the liquid non-spherical droplet.

6. The method according to claim 5, wherein the internal solid material comprises at least about 20%, but no more than about 95%, by volume of the liquid non-spherical droplet.

7. The method according to claim 1, wherein the liquid non-spherical droplet has a circularity of at least one orientation of less than about 0.9.

8. The method according to claim 1, wherein the liquid non-spherical droplet has an aspect ratio of at least one orientation of greater than 1.0.

9. The method according to claim 8, wherein the liquid non-spherical droplet has an aspect ratio of at least one orientation of greater than or equal to 2.0.

10. The method according to claim 9, wherein the liquid non-spherical droplet has an aspect ratio of at least one orientation of greater than or equal to 10.

11. The method according to claim 1, wherein the benefit agent is selected from the group consisting of fabric care agents, home care agents, health care agents, beauty care agents, medicaments, nutraceuticals, and mixtures thereof.

12. The method according to claim 1, wherein the benefit agent is liquid, and:

a) if present in the liquid non-spherical droplet, the droplet liquid/benefit agent mixture has a three-phase contact angle on the internal solid material of less than 1°;

b) if present in the internal solid material, then there is a three-phase contact angle of the droplet liquid on the internal solid material/liquid benefit agent mixture of less than 1°; or c) a combination thereof.

13. The method according to claim 1, wherein the molten ingredient is a wax is selected from the group consisting of synthetic waxes, mineral waxes, hydrocarbon waxes, plant waxes, animal waxes and mixtures thereof.

14. The method according to claim 13, wherein the wax is selected from the group consisting of ozokerite, paraffins, microcrystalline hydrocarbon waxes, petrolatum waxes, castor wax, carnuba wax, beeswax, spermaceti and mixtures thereof.

15. The method according to claim 14, wherein the oil is selected from the group consisting of alkanes, tri-monoglycerides, di-monglycerides, saturated fatty acids, unsaturated fatty acids, sterols, silicone oils, fluorinated oils, mineral oils and mixtures thereof.

16. The method according to claim 14, wherein the alcohol is selected form the group consisting of ethanol, propanol, butanol, pentanol, hexanol and fatty alcohols having a melting point no greater than 25° C.

* * * * *